(12) United States Patent
Kobayashi et al.

(10) Patent No.: US 9,480,746 B2
(45) Date of Patent: Nov. 1, 2016

(54) RESIN CONTAINER FILLED WITH ANTIFUNGAL PHARMACEUTICAL COMPOSITION

(71) Applicants: POLA PHARMA INC., Tokyo (JP); NIHON NOHYAKU CO., LTD., Tokyo (JP)

(72) Inventors: Hirokazu Kobayashi, Yokohama (JP); Madoka Ito, Tokyo (JP); Azuma Nishio, Tokyo (JP)

(73) Assignees: POLA PHARMA INC., Tokyo (JP); NIHON NOHYAKU CO., LTD., Tokyo (JP)

( * ) Notice: Subject to any disclaimer, the term of this patent is extended or adjusted under 35 U.S.C. 154(b) by 0 days.

(21) Appl. No.: 14/257,510

(22) Filed: Apr. 21, 2014

(65) Prior Publication Data

US 2015/0297448 A1 Oct. 22, 2015

(51) Int. Cl.
| | |
|---|---|
| A61K 31/4178 | (2006.01) |
| B65D 81/30 | (2006.01) |
| A61K 47/12 | (2006.01) |
| A61J 1/05 | (2006.01) |
| A61K 31/00 | (2006.01) |
| A61K 47/10 | (2006.01) |
| A61K 47/22 | (2006.01) |

(52) U.S. Cl.
CPC ............ *A61K 47/12* (2013.01); *A61J 1/05* (2013.01); *A61J 1/1418* (2015.05); *A61K 31/00* (2013.01); *A61K 31/4178* (2013.01); *B65D 81/30* (2013.01); *A61J 1/1468* (2015.05); *A61K 47/10* (2013.01); *A61K 47/22* (2013.01)

(58) Field of Classification Search
CPC .......................... A61K 31/4178; B65D 81/30
See application file for complete search history.

(56) References Cited

U.S. PATENT DOCUMENTS

| | | | |
|---|---|---|---|
| 2004/0005419 A1* | 1/2004 | McGrath et al. | 428/35.7 |
| 2006/0229583 A1 | 10/2006 | Nagao et al. | |
| 2009/0030059 A1 | 1/2009 | Miki et al. | |
| 2009/0076109 A1 | 3/2009 | Miki et al. | |
| 2009/0137651 A1 | 5/2009 | Kobayashi et al. | |
| 2010/0210702 A1* | 8/2010 | Vontz et al. | 514/397 |
| 2010/0210703 A1 | 8/2010 | Vontz et al. | |
| 2012/0014893 A1 | 1/2012 | Kobayashi et al. | |
| 2012/0015997 A1 | 1/2012 | Miki et al. | |
| 2012/0022120 A1 | 1/2012 | Kobayashi et al. | |
| 2012/0071533 A1 | 3/2012 | Vontz et al. | |
| 2012/0149745 A1 | 6/2012 | Kobayashi et al. | |
| 2012/0329845 A1* | 12/2012 | Masuda et al. | 514/397 |
| 2013/0096187 A1 | 4/2013 | Kobayashi et al. | |
| 2013/0123318 A1 | 5/2013 | Vontz et al. | |

FOREIGN PATENT DOCUMENTS

| | | |
|---|---|---|
| CN | 1777406 A | 5/2006 |
| JP | 62-178342 A | 8/1987 |
| JP | 63-063751 A | 3/1988 |
| JP | 06-051399 B | 7/1994 |
| JP | 10/077213 A | 3/1998 |
| JP | 10/087472 A | 4/1998 |
| JP | 10/212234 A | 8/1998 |
| JP | 2001-048182 A | 2/2001 |
| JP | 2004-250040 A | 9/2004 |
| JP | 2005-261598 A | 9/2005 |
| JP | 2006-001980 A | 1/2006 |
| JP | 2006-321152 A | 11/2006 |
| JP | 2007-015747 A | 1/2007 |
| JP | 2013-223715 A | 10/2013 |
| WO | WO 2007/102241 A1 | 9/2007 |
| WO | WO 2007/102242 A1 | 9/2007 |
| WO | WO 2007/102243 A1 | 9/2007 |
| WO | WO 2011/024620 A1 | 3/2010 |
| WO | WO 2010/093992 A1 | 8/2010 |
| WO | WO 2010/117089 A1 | 10/2010 |
| WO | WO 2010/117091 A1 | 10/2010 |

OTHER PUBLICATIONS

Kunal et al. (International J. of Pharmaceutical and Chemical Sciences, vol. 1 (3) Jul.-Sep. 2012, p. 1282-1292).*
"Photostability of Drugs and Drug Formulations." Second Edition, Hanne Hjorth Tonnesen, CRC Press, Jun. 29, 2004, 448 pages. Chs. 1-2 provided.*
"Remington: The Science and Practice of Pharmacy." Paul Beringer Ed., 21$^{st}$ edition (2005), 2393 pages. Ch. 52 provided.*
Tonnesen (International Journal of Pharmaceutics 225 (2001) 1-14).*
Sonawane et al. (Arabian Journal of Chemistry (2012), http://dx.doi.org/10.1016/j.arabjc.2012.03.019).*
Office Action issued in corresponding Japanese Patent Application No. 2013-033100, on Jun. 16, 2015.
Office Action issued in corresponding Chinese Patent Application No. 201310087430.7, on May 3, 2016.
Report of Reconsideration by Examiner before Appeal issued in corresponding Japanese Patent Application No. 2013-033100 on Apr. 18, 2016.

* cited by examiner

*Primary Examiner* — Robert Havlin
(74) *Attorney, Agent, or Firm* — Kobbe, Martens, Olson & Bear, LLP

(57) ABSTRACT

Provided is a means for stably storing a pharmaceutical composition comprising a compound represented by the General Formula (I) below and/or a salt thereof, and for providing the pharmaceutical composition to the market. A resin container colored with a color having a hue (H) within the range of 7.0Y to 9.99Y or 7.0YR to 9.99YR, value (V) within the range of 1.0 to 6.0, and chroma (C) within the range of 0.5 to 7.5, according to Munsell color coordinates, is filled with a pharmaceutical composition comprising a compound represented by the General Formula (I) and/or a salt thereof, to store the pharmaceutical composition.

General Formula (I)

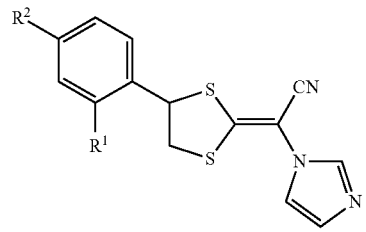

(wherein, in the formula, $R^1$ and $R^2$ each independently represent a hydrogen atom or a halogen atom)

11 Claims, 1 Drawing Sheet

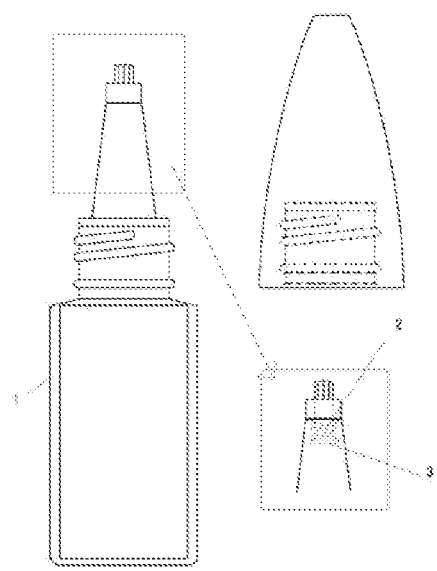

RESIN CONTAINER FILLED WITH ANTIFUNGAL PHARMACEUTICAL COMPOSITION

TECHNICAL FIELD

The present invention relates to a resin container, a resin container filled with an antifungal pharmaceutical composition, more specifically, a colored resin container filled with a pharmaceutical composition containing an antifungal agent.

BACKGROUND ART

Stable and long-term storage of a pharmaceutical composition is an important issue in pharmaceuticals. In cases where a compound having aromaticity is contained as an effective component, it is especially important to secure stability against light. Examples of means for securing stability against light that are commonly carried out include providing of a light blocking structure in a container, such as use of a light-resistant container (see, for example, Patent Document 1). Examples of the light blocking structure generally include structures prepared by mixing a light-blocking metal oxide such as titanium dioxide or zinc oxide in a resin. In cases where such a structure is employed, ultraviolet/visible light hardly reaches the pharmaceutical composition. However, stability of a pharmaceutical composition in a container sometimes cannot be secured even in cases where light is sufficiently blocked by such a light blocking means provided in the container.

Various studies have been carried out on the relationship between light-blocking metal oxides and light in the field of makeup cosmetics, and it has been suggested that light-blocking metal oxides absorb light to become the excited state, and then return to the ground state, generating radicals that impair skin and cosmetics (see, for example, Patent Documents 2 and 3). However, no study has been carried out on the relationship between such radicals and pharmaceutical compositions.

On the other hand, compounds represented by General Formula (I) are known to have excellent antifungal actions, and, in particular, luliconazole, in which both $R^1$ and $R^2$ are chlorine atoms and the absolute configuration of the asymmetric center is (R)-isomer, has a remarkable antifungal action. Further, in terms of problems in their stability, it is known that isomerization proceeds to form the SE isomer, in which the absolute configuration is the (S)-isomer, and the Z isomer, which is a geometric isomer with a double bond (see, for example, Patent Document 4). An important factor that causes such isomerization is light, and the present inventors found that such isomerization cannot be suppressed by normal light blocking means. The present inventors have discovered a means in which use of a container formed with 2 types of layers having different colors prevents such isomerization, but it has not been known that a single-layer container using a resin material having a specific color suppresses such isomerization.

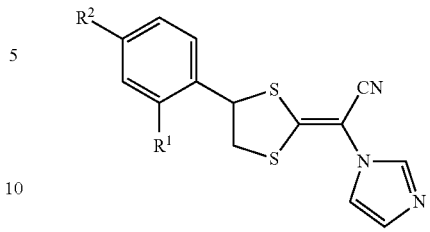

General Formula (I)

(In the formula, $R^1$ and $R^2$ each independently represent a hydrogen atom or a halogen atom.)

On the other hand, the above-described luliconazole has undesirable properties in addition to the problem in the light blocking, such as: 1) poor solubility in solvents; 2) precipitation of crystals on the surface upon application of a highly concentrated solution to the surface of a nail or the like, leading to inhibition of absorption; 3) high tendency to cause stereoisomerization; and the like. Therefore, development of stable and highly effective formulations has been difficult. In particular, in pharmaceutical formulations for onychomycosis, which are required to penetrate into the affected area in a larger amount than formulations for dermatomycosis, there are big problems of low solubility and immediate crystallization upon application (see, for example, Patent Documents 5 and 6), and there is also a big problem in selection of the solvent that allows maintenance of steric properties (see, for example, Patent Document 3). Under these circumstances, N-alkyl-2-pyrrolidones or N-alkyl-2-pyrrolidone related compound such as N-methyl-2-pyrrolidone have been found to be solvents having a steric stabilization action and showing good penetration into the nail. However, in these solvents, the amount of luliconazole that can be dissolved is limited because of the solubility. Therefore, it has been thought that, in normal formulation systems, the upper limit of the amount is less than 3% by mass in cases of a transparent solution.

In terms of highly concentrated formulations of luliconazole, for example, techniques by combination of an alkylene carbonate and a polyol (see, for example, Patent Documents 7 to 9), and formulation using diethylene glycol monoethyl ether (see, for example, Patent Document 10) have achieved formulation of transparent solutions containing luliconazole at a high concentration. However, at present, in N-alkyl-2-pyrrolidone systems, a concentration higher than 3% by mass has not been achieved. If highly concentrated formulations can be achieved in N-alkyl-2-pyrrolidone systems, the effective component can be reduced taking advantage of their excellent penetration into the tissue, so that development of such a technique has been demanded. Further, since such formulations are highly concentrated, the above-described problem in light blocking is more serious. A means for comprehensively solve these problems has been demanded.

PRECEDING TECHNICAL DOCUMENTS

Patent Documents

Patent Document 1: JP 10-212234 A
Patent Document 2: JP 10-87472 A
Patent Document 3: JP 10-77213 A
Patent Document 4: WO2007/102242
Patent Document 5: WO2007/102241

Patent Document 6: WO2007/102243
Patent Document 7: WO2010/117091
Patent Document 8: WO2010/117089
Patent Document 9: WO2011/24620
Patent Document 10: WO2010/93992

SUMMARY OF THE INVENTION

Technical Problem

The present invention was made under these circumstances, and aims to provide a means for stably storing a pharmaceutical composition comprising a compound represented by the General Formula (I) and/or a salt thereof at high concentration even in a container with a single resin layer, for providing the composition to the market.

Solution to Problem

In view of these circumstances, the present inventors intensively studied in order to find a means for stably storing a pharmaceutical composition comprising a compound represented by the General Formula (I) and/or a salt thereof at high concentration, and, as a result, discovered that the stabilization can be achieved by filling, with the pharmaceutical composition, a container colored with a color represented as specific color coordinates, thereby completing the present invention. Further, the present inventors discovered that, by combining an N-alkyl-2-pyrrolidone with benzyl alcohol in a specific amount, an N-alkyl-2-pyrrolidone-based formulation can be obtained as a highly concentrated transparent solution, and that, by filling the above-described colored container with the formulation, a more stable pharmaceutical composition can be provided. That is, the present invention is as follows.

<1> A resin container that can be filled with a content, the resin container comprising a resin surface colored with a color having a hue (H) within the range of 7.0Y to 9.99Y or 7.0YR to 9.99YR, value (V) within the range of 1.0 to 6.0, and chroma (C) within the range of 0.5 to 7.5, according to Munsell color coordinates.

<2> The resin container according to <1>, wherein the resin container does not show permeability in measurement of the ultraviolet-visible absorbance spectrum.

<3> The resin container according to <1> or <2>, wherein material of the resin container is polypropylene or polyethylene.

<4> The resin container according to any one of <1> to <3>, which is a bottle-shaped container.

<5> The resin container according to any one of <1> to <4>, for storing a pharmaceutical composition comprising a compound represented by the General Formula (I) below:

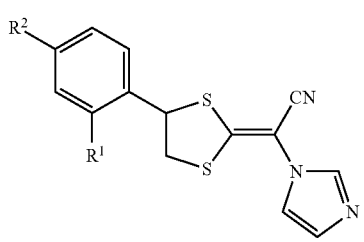

General Formula (I)

(wherein, in the formula, $R^1$ and $R^2$ each independently represent a hydrogen atom or a halogen atom), and/or a salt thereof.

<6> A pharmaceutical prepared by filling the resin container according to any one of <1> to <5> with a pharmaceutical composition comprising a compound represented by the General Formula (I) below:

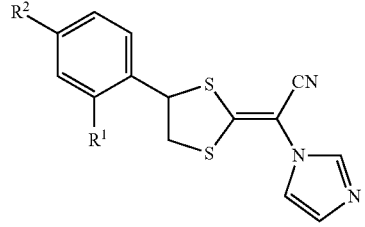

General Formula (I)

(wherein, in the formula, $R^1$ and $R^2$ each independently represent a hydrogen atom or a halogen atom), and/or a salt thereof.

<7> The pharmaceutical according to <6>, wherein the compound represented by General Formula (I) is luliconazole.

<8> The pharmaceutical according to <6> or <7>, wherein the pharmaceutical composition is in the form of a lotion.

<9> The pharmaceutical according to any one of <6> to <8>, wherein the pharmaceutical composition comprises: 1) 3 to 8% by mass of luliconazole; 2) 1 to 3% by mass of benzyl alcohol; and 3) 6 to 15% by mass of solvent selected from N-methyl-2-pyrrolidone, propylene carbonate and an ether of diethylene glycol in total; and is a transparent solution.

<10> The pharmaceutical according to <9>, wherein the pharmaceutical composition further comprises 10 to 16% by mass of a diester of a dibasic acid.

<11> The pharmaceutical according to <9> or <10>, wherein the pharmaceutical composition further comprises 3 to 6% by mass of an organic acid.

<12> The pharmaceutical according to <11>, wherein the organic acid is lactic acid.

<13> The pharmaceutical according to any one of <9> to <12>, wherein the pharmaceutical composition has the following physical properties:

1) crystallization does not occur under storage conditions at room temperature for 3 years;

2) the content of the SE isomer of luliconazole is not more than 0.5% by mass with respect to the amount of luliconazole added;

3) the content of the Z isomer of luliconazole is not more than 0.5% by mass with respect to the amount of luliconazole added;

4) the amount of the SE isomer produced is not more than 0.2% by mass with respect to the amount of luliconazole added, under storage conditions at 40° C. for 6 months;

5) the amount of the Z isomer produced is not more than 0.2% by mass with respect to the amount of luliconazole added, under storage conditions at 40° C. for 6 months; and 6) crystallization does not occur on a nail immediately after application to the nail.

<14> The pharmaceutical according to any one of <11> to <13>, wherein the pharmaceutical composition is produced by:

wetting luliconazole with a part of the solvent selected from N-methyl-2-pyrrolidone, propylene carbonate and an ether of diethylene glycol;

adding benzyl alcohol and an organic acid to, and dispersing, the wet luliconazole; and then adding the remaining components.

<15> A pharmaceutical composition that is a transparent solution comprising: 1) 3 to 8% by mass of luliconazole; 2) 1 to 3% by mass of benzyl alcohol; and 3) 6 to 15% by mass of N-methyl-2-pyrrolidone.

<16> The pharmaceutical composition according to <15>, further comprising 10 to 16% by mass of a diester of a dibasic acid.

<17> The pharmaceutical composition according to <15> or <16>, further comprising 3 to 6% by mass of an organic acid.

<18> The pharmaceutical composition according to <17>, wherein the organic acid is lactic acid.

<19> The pharmaceutical composition according to any one of <15> to <18>, having the following physical properties:

1) crystallization does not occur under storage conditions at room temperature for 3 years;

2) the content of the SE isomer of luliconazole is not more than 0.5% by mass with respect to the amount of luliconazole added;

3) the content of the Z isomer of luliconazole is not more than 0.5% by mass with respect to the amount of luliconazole added;

4) the amount of the SE isomer produced is not more than 0.2% by mass with respect to the amount of luliconazole added, under storage conditions at 40° C. for 6 months;

5) the amount of the Z isomer produced is not more than 0.2% by mass with respect to the amount of luliconazole added, under storage conditions at 40° C. for 6 months; and 6) crystallization does not occur on a nail immediately after application to the nail.

<20> The pharmaceutical composition according to any one of <17> to <19>, produced by:

wetting luliconazole with a part of the N-methyl-2-pyrrolidone;

adding benzyl alcohol and an organic acid to, and dispersing, the wet luliconazole; and then adding the remaining components.

Advantageous Effects of Invention

By the present invention, a pharmaceutical composition stably comprising a compound represented by the General Formula (I) and/or a salt thereof at high concentration, a resin container that enables stable storage of the pharmaceutical composition even in cases where the container has only a single resin layer, and a pharmaceutical filled in the resin container that can stably store the pharmaceutical composition, can be provided to the market.

BRIEF DESCRIPTION OF DRAWINGS

FIG. 1 illustrates the structure of the container used in Examples. The numerals represent: 1, resin wall surface; 2, lifting structure composed of an elastic body; and 3, movable stopper.

DESCRIPTION OF EMBODIMENTS

<1> Resin Container

The resin container of the present invention is described below in detail with reference to FIG. 1, which illustrates an embodiment of the container. The embodiment illustrated in FIG. 1 is a resin container that can be filled with a content and comprises a resin wall surface 1, a lifting structure composed of an elastic body 2, and a movable stopper 3. The inside of the container provided by the resin wall surface 1 can contain a content. The resin wall surface 1 is colored with a color having a hue (H) within the range of 7.0Y to 9.99Y or 7.0YR to 9.99YR, value (V) within the range of 1.0 to 6.0, and chroma (C) within the range of 0.5 to 7.5, according to Munsell color coordinates.

The resin container of present invention is characterized in that the resin surface is colored, and the coloring is an indispensable constituent. The coloring is carried out with a specific color. That is, coloring with a color having a hue (H) within the range of 7.0Y to 9.99Y or 7.0YR to 9.99YR, more preferably 7.3Y to 9.8Y or 7.3YR to 9.8YR, value (V) within the range of 1.0 to 6.0, more preferably 1.5 to 5.5, and chroma (C) within the range of 0.5 to 7.5, preferably 0.5 to 6, according to Munsell color coordinates, is a constituent of the present invention. More specifically, the color is preferably gray, green or brown, and, according to Munsell color coordinates, preferred examples of the color include gray colors having a hue within the range of 7.0Y to 8.6Y, value within the range of 4.0 to 6.0, and chroma within the range of 0.5 to 1.0; green colors having a hue within the range of 9.0Y to 9.9Y, value within the range of 1.5 to 2.5, and chroma within the range of 6 to 7.5; and brown colors having a hue within the range of 8YR to 9YR, value within the range of 1.5 to 2.0, and chroma within the range of 4 to 5. Possible examples of the pigment for carrying out such coloring include white pigments such as titanium dioxide and zinc oxide; black pigments such as iron black; red pigments such as colcothar, toluidine red and quinacridone red; blue pigments such as ultramarine, prussian blue and phthalocyanine blue; green pigments such as phthalocyanine green, chrome green and cadmium green; and yellow pigments such as yellow iron oxide and azo yellow.

The term "Munsell color coordinates" herein means a colorimetric system devised by H. A. Munsell, which expresses colors using three axes, that is, value (V), chroma (C) and hue (H). Munsell color coordinates are said to be excellent in expression of the human sense of color recognition using coordinate values. It is generally known that colors can be expressed with combinations of 3 independent stimulus values, and examples of such combinations also include the RGB colorimetric system and XYZ colorimetric system. However, it is said that the chromaticity coordinates of the Munsell colorimetric system most easily allow one to image colors (The Color Science Association of Japan, ed., "Handbook of color science, new edition", University of Tokyo Press, Sep. 10, 1985).

The resin container provides light blocking as a constituent. The light blocking in the present invention means that the resin container does not show permeability in measurement of the ultraviolet-visible absorbance spectrum. More specifically, when a resin piece of the resin container is placed in a UV-VIS spectrophotometer and the UV absorbance and the visible absorbance are measured, the transmittance is not more than 5%, preferably 0% in both cases.

For example, the measurement of the UV-VIS absorbance spectrum can be carried out using a UV-VIS spectrophotometer (V-660: manufactured by JASCO Corporation) at wavelengths of 200 to 750 nm.

That is, in the resin container of the pharmaceutical of the present invention, coloring of at least a part of the resin surface, preferably the contact surface with the content, with a specific color; and having a light blocking effect; can be said to be indispensable constituents. Conventionally, multilayer structures are employed for containers in order to give various functions. In the present invention, within the color range described above, a pharmaceutical composition comprising a compound represented by the General Formula (I) and/or a salt thereof can be stably stored even in cases where the resin layer constituting the resin container is a single layer. Accordingly, a layer for adding a color or the like may be placed outside such a colored surface, and such an embodiment is also within the technical scope of the present invention. Even with sufficient light blocking, in cases where the color is not within the color range described above, pharmaceutical compositions cannot be stably stored in some cases. Thus, it can be assumed that the stability of the pharmaceutical composition contained in the resin container of the present invention is due to a secondary or indirect action via the container or the like, rather than a direct action of the light. Such a decrease in the stability caused by an action other than a direct action of light is not generally known. Therefore, under these circumstances, the effect to maintain stability of the pharmaceutical composition achieved by coloring the container with a specific color is a special effect. The resin container of the present invention is characterized in that it has such an effect.

The shape of the container may be one that is usually employed for pharmaceuticals, as long as the above-described conditions are satisfied.

Preferred examples of the shape include bottle shapes, tubular shapes and jar shapes, and, in view of filling the container with a pharmaceutical composition of the present invention, bottle shapes are especially preferred.

Further, a preferred example of the shape is a bottle shape having a structure that opens by pressing against an affected area as shown in FIG. 1. That is, the bottle shape of FIG. 1 is a bottle shape in which a secondary chamber is provided in the tip portion and a structure that is to be opened and closed by an elastic body (a lifting structure composed of an elastic body, and a movable stopper) is provided in the joint section between the secondary chamber and the drug storage portion in the main body of the container, wherein this structure is usually closed by the elastic body, and it is opened by pressing a rod-shaped pressing section as the part contacting with the affected area. In the rod-shaped pressing section, a plurality of longitudinal grooves are provided, and, when the joint section is opened by pressing the rod-shaped pressing section against the affected area, the drug stored in the drug storage portion in the main body of the container flows into the secondary chamber, followed by further flowing through the groove sections to be continuously supplied to the affected area in a predetermined amount.

Preferred examples of the material of the container include polyethylene, polypropylene, polyethylene terephthalate, acrylic resin, polyester and polyamide, and, in view of filling the container with a pharmaceutical composition of the present invention, the material is preferably polyethylene or polypropylene, more preferably polyethylene. Such resins may contain metal oxides such as titanium dioxide and zinc oxide, for the purpose of light blocking.

Preferably, from the viewpoint of the cost, only a single layer is provided as a colored layer in view of both the production cost and the production method.

The method for producing a container may be one that is usually employed for containers for pharmaceuticals, as long as the above-described conditions are satisfied. For example, the colored resin surface of the resin container may be prepared by coloring the resin itself or coloring the inside of the resin with a coloring agent that does not affect the pharmaceutical composition.

As the coloring agent, the above-described coloring agents and the like may be used.

<2> Pharmaceutical Composition

The pharmaceutical composition with which the resin container of the present invention is preferably filled is characterized in that it contains a compound represented by the General Formula (I) and/or a salt thereof. Preferred examples of the compound represented by General Formula (I) include lanoconazole, in which $R^1$ is a chlorine atom and $R^2$ is a hydrogen atom, and luliconazole, in which both $R^1$ and $R^2$ are chlorine atoms. Either of these may be contained in the pharmaceutical composition. Methods for producing these components are already known (e.g., JP 09-100279 A). In these pharmaceutical compositions, the content of the compound represented by General Formula (I) and/or a salt thereof is preferably 0.1 to 20% by mass, more preferably 0.2 to 10% by mass. This is because an amount within these ranges allows maintenance of the stability. In particular, in cases where the pharmaceutical composition is used as a formulation for nails, it is preferably a transparent and uniform solution, and the concentration of the compound represented by General Formula (I) is preferably high. More specifically, especially preferred examples of the pharmaceutical composition include those using an N-alkyl-2-pyrrolidone as a solvent and containing the compound represented by General Formula (I) at 3 to 8% by mass, more preferably 4 to 6% by mass, with respect to the total amount of the pharmaceutical composition. Further, the effect of the container of the present invention covers propylene carbonate and an ether of diethylene glycol such as diethylene glycol monoethyl ether and diethylene glycol diethyl ether which provide the same effect of stably dissolving luliconazole with N-alkyl-2-pyrrolidones. Therefore, those solvents are also used as well as N-alkyl-2-pyrrolidones.

Examples of formulations applicable to the pharmaceutical composition include not only nail formulations but also other formulations that are usually used as pharmaceuticals. Specific examples of the formulations in such cases include emulsified or solubilized lotions, emulsions, creams and ointments. Among these, lotions are especially preferred. This is because lotions often have especially serious problems in stability against light or the like.

The pharmaceutical composition of the present invention is characterized in that it contains an N-alkyl-pyrrolidone, and characterized in that it utilizes excellent actions of N-alkyl-2-pyrrolidones including N-methyl-2-pyrrolidone on luliconazole, such as excellent penetration into the nail and a steric-stability-improving action. In this sense, containing an N-alkyl-2-pyrrolidone is an indispensable constituent. The N-alkyl-2-pyrrolidone preferably has an alkyl group having 1 to 4 carbon atoms, and preferred examples of the N-alkyl-2-pyrrolidone include N-methyl-2-pyrrolidone, N-ethyl-2-pyrrolidone, N-propyl-2-pyrrolidone and N-butyl-2-pyrrolidone. The carbon chain of the alkyl group is more preferably short, and, more specifically, N-methyl- 2-pyrrolidone, N-ethyl-2-pyrrolidone, N-propyl-2-pyrrolidone and N-butyl-2-pyrrolidone are preferred in that order. Only one of these components may be contained, or two or more of these may be contained in combination. In the pharmaceutical composition of the present invention, the total content of N-alkyl-2-pyrrolidone is preferably 6 to 15% by mass, more preferably 7 to 12% by mass, with respect to the total amount of the pharmaceutical composition. This is because, in cases where the content is too low, the preferred properties of N-alkyl-2-pyrrolidone may not be obtained, while in cases where the content is too high, undesirable phenomena such as crystallization may occur.

An indispensable constituent of the pharmaceutical composition of the present invention is to contain 1 to 3% by mass, preferably 1 to 2% by mass of a hydroxyalkylbenzene such as benzyl alcohol, in addition to the N-alkyl-2-pyrrolidone. Hydroxyalkylbenzenes such as benzyl alcohol have an action to solubilize luliconazole, but, on the other hand, in cases where they are processed into formulation systems, they have properties that easily induce crystallization during storage at low temperature. By controlling the amount within the range described above, such a problem of crystallization can be solved, and a highly concentrated formulation can be realized. That is, both in cases where the content of hydroxyalkylbenzene such as benzyl alcohol added is lower than the above-described range, and in cases where its content is higher than the above-described range, resulting in failure to obtain a formulation having a practical solution stability and having the content of luliconazole over 3% by mass.

The hydroxyalkylbenzene preferably has an alkyl group having 1 to 4 carbon atoms, and preferred specific examples of the hydroxyalkylbenzene include benzyl alcohol, phenethyl alcohol, phenylpropanol and phenylbutanol. Only one of these components may be contained, or two or more of these may be contained in combination. The hydroxyalkylbenzene is especially preferably benzyl alcohol or phenethyl alcohol, more preferably benzyl alcohol. By inclusion of the hydroxyalkylbenzene at the above-described content, the action to stabilize the solution state and to prevent crystallization can be exerted during storage of the compound represented by the General Formula (I) and/or a salt thereof in a low temperature range, for example, at about 5° C.

In a preferred mode, the pharmaceutical composition of the present invention is characterized in that it contains a diester of a dibasic acid. In the present invention, diester carbonate is not included in the diester of a dibasic acid. Especially preferred examples of the diester of a dibasic acid include diethyl adipate, diisopropyl adipate, diethyl sebacate and dipropyl sebacate. Among these, diisopropyl adipate is especially preferred. These components have an action to prevent crystallization in a luliconazole solution containing benzyl alcohol at low temperature. This action complements solubility of luliconazole by the N-alkyl-2-pyrrolidone. In order to realize this action, the total content of the diester of a dibasic acid is preferably 10 to 16% by mass, more preferably 12 to 14% by mass with respect to the total amount of the pharmaceutical composition.

In a preferred mode, the pharmaceutical composition of the present invention is characterized in that it contains 3 to 6% by mass, more preferably 4 to 5% by mass of an organic acid. The organic acid is preferably an α-hydroxy acid. Among α-hydroxy acids, lactic acid and glycolic acid are more preferred. These components are excellent in an action to suppress phenomena such as immediate crystallization upon application of the pharmaceutical composition to the surface of a nail. Further, these components similarly realize actions to suppress crystallization during storage at low temperature and to suppress the tendency due to storage at low temperature to cause crystallization upon application. By this, the pharmaceutical composition of the present invention can realize excellent tissue penetration without inhibition of its properties.

In addition to the above components, the pharmaceutical composition of the present invention may contain components usually used for pharmaceutical compositions. Examples of such components include alcohols such as ethanol; coating agents such as polyvinylpyrrolidone and methylcellulose; moisturizers such as propylene glycol and polyethylene glycol; stabilizers such as phosphate; and solvents such as methyl ethyl ketone and medium-chain triglycerides. The pharmaceutical composition of the present invention can be produced by combining these indispensable components and arbitrary components, and then processing the resulting combination according to a conventional method.

The pharmaceutical composition of the present invention can be preferably produced by the following production method.

Luliconazole is wetted with a part of N-methyl-2-pyrrolidone (for example, 1 to 5% by mass with respect to the total amount of pharmaceutical composition), and benzyl alcohol and an organic acid are added thereto, thereby dispersing the wet luliconazole and then adding the remaining components to the resulting dispersion.

Further, taking advantage of the property of the composition to show excellent penetration into the nail tissue, the composition can be used as a pharmaceutical composition for onychomycosis.

That is, the pharmaceutical or pharmaceutical composition of the present invention is preferably used for treatment, or prevention of exacerbation, of a fungus disease(s), utilizing properties of the compound represented by the General Formula (I) and/or a salt thereof. Examples of the fungus diseases include tinea pedis such as athlete's foot; tinea corporis such as candidiasis and tinea versicolor; and trichophytosis in hard keratin areas such as tinea unguium. Since the effect is remarkable, the pharmaceutical or pharmaceutical composition of the present invention is especially preferably used for treatment of hard keratin areas such as tinea unguium. Although the effect of the pharmaceutical composition of the present invention is especially preferably produced in nails, it also covers normal dermatomycosis, so that pharmaceutical compositions for dermatomycoses that satisfy the constitution of the present invention are also within the scope of the present invention. Examples of such dermatomycoses include tinea pedis, and tinea pedis such as trichophytosis with hyperkeratosis that appears on the heel and the like. Among the above dermatomycoses, application to trichophytosis with hyperkeratosis, for which normal drugs are less effective, is preferred since the effect of the present invention is remarkably produced thereby.

The mode of use may be appropriately selected in consideration of the body weight, age, sex, symptoms and the like of the patient, and, in adult human, the daily dose of the compound represented by General Formula (I) and/or a salt thereof is usually 0.01 to 1 g. Further, one may refer to doses of compounds represented by General Formula (I) and salts thereof that are normally used for diseases caused by fungi.

For example, in cases of an external preparation, it may be applied in an appropriate amount to the affected area once or several times per day, and such treatment is preferably carried out every day. In particular, in cases of tinea unguium, luliconazole in an amount that cannot be realized with a normal preparation can be transferred into the nail. By this, tinea unguium can be treated by only external application, without long-term oral administration of an antifungal agent. In tinea unguium, recurrence and reinfection are big problems. By administering a pharmaceutical composition of the present invention for 1 or 2 weeks after disappearance of symptoms, such recurrence and reinfection can be prevented. The pharmaceutical composition of the present invention produces the prophylactic effect in such a mode.

The pharmaceutical of the present invention can stably maintain a compound represented by the General Formula (I) and/or a salt thereof at high concentration, and, in one embodiment, the pharmaceutical of the present invention has any one or more, or all, of the following physical properties 1) to 6).

1) Crystallization does not occur under storage conditions at room temperature for 3 years.

2) The content of the SE isomer of luliconazole is not more than 0.5% by mass with respect to the amount of luliconazole added.

3) The content of the Z isomer of luliconazole is not more than 0.5% by mass with respect to the amount of luliconazole added.

4) The amount of the SE isomer produced is not more than 0.2% by mass with respect to the amount of luliconazole added, under storage conditions at 40° C. for 6 months.

5) The amount of the Z isomer produced is not more than 0.2% by mass with respect to the amount of luliconazole added, under storage conditions at 40° C. for 6 months.

6) Crystallization does not occur on a nail immediately after application to the nail.

The crystallization can be measured by visual observation.

The contents of isomers of luliconazole can be determined by, for example, optical resolution of luliconazole and its isomers by liquid chromatography using an optically active stationary phase that is capable of separating them, followed by calculating the areas of peaks for the optical isomers in the obtained chart.

(3) Pharmaceutical

The pharmaceutical of the present invention is a pharmaceutical prepared by filling the resin container of the present invention with a pharmaceutical composition comprising a compound represented by the General Formula (I) and/or a salt thereof.

In the resin container of the present invention, the compound represented by the General Formula (I) and/or a salt thereof can be stably maintained at high concentration. Therefore, the pharmaceutical of the present invention is a pharmaceutical prepared by filling the resin container of the present invention with the pharmaceutical composition of the present invention comprising a compound represented by the General Formula (I) and/or a salt thereof at high concentration in the above-described specific composition.

EXAMPLES

The present invention is described in more detail by way of Examples, but the present invention is not limited to these Examples.

Example 1

According to the formulation shown in Table 2, a pharmaceutical composition of the present invention was produced. That is, luliconazole was wetted with methyl ethyl ketone, and polyethylene glycol was added thereto, thereby uniformly dispersing it. Subsequently, the remaining part was added to the dispersion, and the resultant was dissolved under heat, followed by cooling the resulting solution to obtain a pharmaceutical composition of the present invention. The amounts of the SE isomer and the Z isomer, which are impurities of luliconazole, produced were measured by high-performance liquid chromatography (conditions: column, Inertsil ODS-2 4.6×150 mm; column temperature, 40° C.; mobile phase, 0.13% sodium 1-undecanesulfonate mixture (water/acetonitrile/acetic acid 54:45:1, v/v/v) solution; flow rate, 1.0 mL/min; detection, 295 nm).

The following containers having the properties shown in Table 1 were prepared. That is, titanium dioxide as a white pigment; yellow iron oxide as a yellow pigment; prussian blue and phthalocyanine blue as blue pigments; phthalocyanine green and chrome green as green pigments; quinacridone red and colcothar as red pigments; and black iron oxide as a black pigment; were used. Pigments were added at 2% by mass with respect to the total amount of resin, and each color of interest was achieved by adjusting the color by appropriately changing the pigment ratio. The pigment was added to a molten resin, and the container was prepared by blow hollow molding.

The wall surface of the container material, containing a colored resin surface, was subjected to measurement of the UV-VIS absorbance spectrum (V-660: manufactured by JASCO Corporation; 200 to 750 nm).

The container was filled with the pharmaceutical composition shown in Table 2, and light irradiation tests were carried out under the 2 conditions described below. After completion of the tests, the pharmaceutical composition was removed. The amounts of the SE isomer and the Z isomer as impurities of luliconazole produced were measured by high-performance liquid chromatography, and properties of the liquid was visually observed. The results are shown in Table 3.

From the results shown in Table 3, it can be seen that pharmaceutical composition of the present invention contained in the sample Nos. 1 to 3, which are the gray, brown and green containers, respectively, shows excellent photostability in the dark provided by the containers. It can also be seen that, since the transmittance of the ultraviolet-visual light was 0% in all samples, such an effect cannot be produced only by light blocking.

<Conditions for Light Irradiation Test 1>
White fluorescent lamp: white fluorescent lamp National FLR-20S•W/M
Total illuminance: 1,200,000 lx/h
Illuminance setting: 5 klx
Number of days of irradiation: 10 days
<Conditions for Light Irradiation Test 2>
Near-ultraviolet fluorescent lamp: fluorescent chemical lamp FLR-20S•BL/M-(A)
Total near-ultraviolet radiant energy: 200 W/h/m$^2$
Ultraviolet intensity setting: 15 W/m$^2$
Irradiation time: 13.5 hours

TABLE 1

| Sample No. | Color (hue, value/chroma) | Material (thickness) | Transmittance of ultraviolet-visual light |
|---|---|---|---|
| Sample 1 | Gray (7.56Y, 5.0/0.7) | PE (1.2 mm) | 0% |
| Sample 2 | Green (9.46Y, 2.1/7.2) | PE (1.2 mm) | 0% |

TABLE 1-continued

| Sample No. | Color (hue, value/chroma) | Material (thickness) | Transmittance of ultraviolet-visual light |
|---|---|---|---|
| Sample 3 | Brown (8.4YR, 1.7/4.2) | PE (1.2 mm) | 0% |
| Sample 4 | White (2.16Y, 9.8/3.8) | PE (1.2 mm) | 0% |
| Sample 5 | Blue (3.6PB, 2.0/8.0) | PE (1.2 mm) | 0% |

In this Table, PE means polyethylene.

TABLE 2

| Formulation component | Mass % |
|---|---|
| Luliconazole | 1.0 |
| Propylene glycol | 20 |
| Medium-chain triglyceride | 25 |
| Methyl ethyl ketone | 5 |
| Phosphoric acid | Appropriate amount (added to pH 5.5) |
| Ethanol | Remaining amount |

TABLE 3-1

| Impurity | Sample No. | Initial | Light irradiation test condition 1 | Light irradiation test condition 2 |
|---|---|---|---|---|
| SE isomer | Sample 1 | 0.28 | 0.29 | 0.29 |
| | Sample 2 | 0.28 | 0.26 | 0.27 |
| | Sample 3 | 0.28 | 0.27 | 0.27 |
| | Sample 4 | 0.28 | 0.29 | 0.29 |
| | Sample 5 | 0.28 | 0.28 | 0.29 |
| Z isomer | Sample 1 | 0.02 | 0.02 | 0.02 |
| | Sample 2 | 0.02 | 0.02 | 0.02 |
| | Sample 3 | 0.02 | 0.02 | 0.02 |
| | Sample 4 | 0.02 | 0.87 | 0.76 |
| | Sample 5 | 0.02 | 1.20 | 3.56 |

In this Table, the SE isomer and the Z isomer as impurities are represented by the structural formulae below.

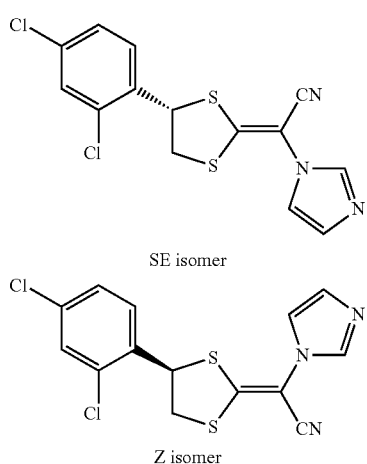

SE isomer

Z isomer

TABLE 3-2

| Sample No. | |
|---|---|
| Sample 1 | Transparent, colorless |
| Sample 2 | Transparent, colorless |
| Sample 3 | Transparent, colorless |

TABLE 3-2-continued

| Sample No. | |
|---|---|
| Sample 4 | Transparent, pale yellow |
| Sample 5 | Transparent, colorless |

Example 2

According to the formulation shown in Table 4, the pharmaceutical composition 1 of the present invention was produced. That is, the total amount of luliconazole was wetted with a part of N-methyl-2-pyrrolidone, and the total amount of benzyl alcohol was added thereto. Lactic acid was further added to the resulting mixture, and the remaining N-methyl-2-pyrrolidone and the total amount of diisopropyl adipate were added thereto. After sufficiently mixing the resulting mixture by stirring, ethanol and polyvinyl pyrrolidone were added to the mixture, and the resulting mixture was mixed under heat for solubilization, followed by allowing the resulting solution to cool to room temperature with stirring, to obtain the pharmaceutical composition 1 of the present invention. The content of the SE isomer immediately after production of this composition was 0.27% by mass, and the content of the SE isomer in the sample after storage at 40° C. for 6 months was 0.27% by mass. Therefore, additional SE isomers were hardly produced. In terms of the Z isomer, the content immediately after production was 0.03% by mass, and the content of the SE isomer in the sample after storage at 40° C. for 6 months was 0.05% by mass. Therefore, the amount of the isomer produced during the storage was 0.02% by mass. Even after 9 months of a long-term storage test at room temperature, no crystallization was found. In general, results of 6 months of a long-term storage test at 40° C., and results of 9 months of a long-term storage test at room temperature, are similar to results of 3 years of storage at room temperature, so that these results can be regarded as results of 3 years of storage at room temperature. Further, no crystallization was found on the nail upon use. Therefore, this formulation was found to be satisfying the conditions 1) to 6) below.

1) Crystallization does not occur under storage conditions at room temperature for 3 years.

2) The content of the SE isomer of luliconazole is not more than 0.5% by mass with respect to the amount of luliconazole added.

3) The content of the Z isomer of luliconazole is not more than 0.5% by mass with respect to the amount of luliconazole added.

4) The amount of the SE isomer produced is not more than 0.2% by mass with respect to the amount of luliconazole added, under storage conditions at 40° C. for 6 months.

5) The amount of the Z isomer produced is not more than 0.2% by mass with respect to the amount of luliconazole added, under storage conditions at 40° C. for 6 months.

6) Crystallization does not occur on a nail immediately after application to the nail.

By this, it can be seen that this formulation maintains properties of N-methyl-2-pyrrolidone such as excellent penetration into the nail and the steric-stability-improving action.

Further, as also shown in Reference Examples 1 and 2 below, in compositions containing 8% by mass of N-methyl-2-pyrrolidone, it is difficult to stably dissolve even 3% by mass of luliconazole. However, it can be seen that the pharmaceutical composition of the present invention can stably dissolve 5% by mass of luliconazole.

TABLE 4

| Formulation component | Mass % |
| --- | --- |
| Luliconazole | 5 |
| Benzyl alcohol | 2 |
| Diisopropyl adipate | 10 |
| N-methyl-2-pyrrolidone | 8 |
| Lactic acid | 4 |
| Polyvinyl pyrrolidone | 0.5 |
| Ethanol | Remaining amount |

Example 3

According to the formulation shown in Table 5, the pharmaceutical compositions 2 to 4 of the present invention were produced in the same manner as in Example 2. These exhibited properties as a transparent solution immediately after the production. A long-term storage test was carried out at room temperature for 9 months, and the extent of crystallization was visually investigated. The results are also shown in Table 5. By this, it can be seen that the preferred content of benzyl alcohol is 1 to 3% by mass, more preferably 1 to 2% by mass.

TABLE 5

| | Mass % | | |
| --- | --- | --- | --- |
| Formulation component | Pharmaceutical composition 2 | Pharmaceutical composition 3 | Pharmaceutical composition 4 |
| Luliconazole | 5 | 5 | 5 |
| Benzyl alcohol | 1 | 1.5 | 3 |
| Diisopropyl adipate | 10 | 10 | 10 |
| N-methyl-2-pyrrolidone | 8 | 8 | 8 |
| Lactic acid | 4 | 4 | 4 |
| Polyvinyl pyrrolidone | 0.5 | 0.5 | 0.5 |
| Ethanol | Remaining amount | Remaining amount | Remaining amount |
| Degree of crystallization after storage at room temperature for 9 months | Slight crystallization | No change in properties | Crystallization at low level |

Example 4

According to the formulation shown in Table 6, the pharmaceutical compositions 5 and 6 of the present invention were produced in the same manner as in Example 2. These exhibited properties as a transparent solution immediately after the production. A long-term storage test was carried out at room temperature for 9 months, and the extent of crystallization was visually investigated. The results are also shown in Table 6. By this, it can be seen that the preferred content of diisopropyl adipate is 11 to 16% by mass, more preferably 11 to 14% by mass.

TABLE 6

| | Mass % | |
| --- | --- | --- |
| Formulation component | Pharmaceutical composition 5 | Pharmaceutical composition 6 |
| Luliconazole | 5 | 5 |
| Benzyl alcohol | 2 | 2 |
| Diisopropyl adipate | 11 | 14 |
| N-methyl-2-pyrrolidone | 8 | 8 |
| Lactic acid | 4 | 4 |
| Polyvinyl pyrrolidone | 0.5 | 0.5 |
| Ethanol | Remaining amount | Remaining amount |
| Degree of crystallization after storage at room temperature for 9 months | Slight crystallization | No change in properties |

Example 5

The container of Sample 1 in Example 1 was filled with the pharmaceutical composition 1 of Example 2, to provide a pharmaceutical of the present invention. This was stable in a storage test at 40° C. for 6 months in spite of the fact that it contained luliconazole at high concentration.

Reference Example 1

According to the formulation shown in Table 7, a luliconazole preparation was prepared. That is, benzyl alcohol was added to luliconazole, and luliconazole was dissolved, followed by adding ethanol, diisopropyl adipate, N-methyl-2-pyrrolidone and lactic acid in that order. The resulting mixture was heated for solubilization, and the resulting solution was then allowed to cool to room temperature, to obtain a preparation having properties as a transparent solution. This solution was stored at 5° C. for 2 weeks, and, as a result, crystallization occurred. In this system, the amount of benzyl alcohol is larger than the range in the present invention, and it can be seen that the upper limit of the amount of luliconazole added is less than 3% by mass.

TABLE 7

| Formulation component | Mass % |
| --- | --- |
| Luliconazole | 3 |
| Benzyl alcohol | 4 |
| Diisopropyl adipate | 10 |
| N-methyl-2-pyrrolidone | 8 |
| Lactic acid | 4 |
| Polyvinyl pyrrolidone | 0.5 |
| Ethanol | Remaining amount |

Reference Example 2

According to the formulation shown in Table 8, a pharmaceutical composition having properties as a transparent solution was obtained by the same operation as in Reference Example 1. This composition showed crystallization after storage at 5° C. for 12 weeks. Thus, it can be seen that, in a luliconazole solution formulation containing an N-alkyl- 2-pyrrolidone in which the amount of benzyl alcohol is larger than the range in the present invention, the upper limit of the amount of luliconazole added is 3% by mass.

TABLE 8

| Formulation component | Mass % |
|---|---|
| Luliconazole | 3 |
| Benzyl alcohol | 4 |
| Isopropyl myristate | 10 |
| N-methyl-2-pyrrolidone | 8 |
| Lactic acid | 4 |
| Polyvinyl pyrrolidone | 0.5 |
| Ethanol | Remaining amount |

Example 6

The pharmaceutical composition 7 was prepared according to Table 9 below in the same manner as the pharmaceutical composition 1. The container of Sample 1 in Example 1 was filled with this composition, and stored at 60° C. or 40° C. to investigate its stability. The results are shown in Table 10. By this, it can be seen that the pharmaceutical composition 7 shows excellent stability in a state where it is contained in the container of Sample 1 in Example 1.

TABLE 9

| Component name | Amount added (mass %) |
|---|---|
| Luliconazole | 5.0 |
| N-methyl-2-pyrrolidone | 8.0 |
| Benzyl alcohol | 2.0 |
| Diisopropyl adipate | 12.0 |
| Lactic acid | 4.0 |
| Povidone | 0.5 |
| Absolute ethanol | 68.5 |

TABLE 10

| Evaluation item | Initial | 60° C., 3 weeks | 40° C., 1 month |
|---|---|---|---|
| S-E isomer (mass %) | 0.02 | 0.04 | 0.03 |
| Z isomer (mass %) | 0.00 | 0.05 | 0.01 |
| Total amount of other related substances (mass %) | 0.00 | 0.06 | 0.00 |
| Content (%) | 100.13 | 102.79 | 101.95 |

While the invention has been described in detail with reference to preferred embodiments thereof, it will be apparent to one skilled in the art that various changes can be made, and equivalents employed, without departing from the scope of the invention. Each of the aforementioned documents, including the foreign document, JP Application No. 2012-61536, JP Application No. 2013-33100 (JP 2013-223715 A) is incorporated by reference herein in its entirety.

INDUSTRIAL APPLICABILITY

The present invention can be applied to pharmaceuticals.

DESCRIPTION OF SYMBOLS

1 . . . Resin wall surface
2 . . . Lifting structure composed of an elastic body
3 . . . Movable stopper.

The invention claimed is:

1. A pharmaceutical prepared by filling a resin container with a pharmaceutical composition comprising luliconazole and/or a salt thereof, wherein said resin container has light blocking effect and comprising a resin surface colored with a color having a hue (H) within the range of 7.0Y to 9.99Y or 7.0YR to 9.99YR, value (V) within the range of 1.0 to 6.0, and chroma (C) within the range of 0.5 to 7.5, according to Munsell color coordinates, wherein the Z-isomer of luliconazole is present at less than 0.02% after light irradiation of luliconazole in the resin container for 10 days under a white fluorescent lamp at 5 klx and 1,200,000 lx/h.

2. The pharmaceutical according to claim 1, wherein said pharmaceutical composition is in the form of a lotion.

3. The pharmaceutical according to claim 1, wherein said pharmaceutical composition comprises: 1) 3 to 8% by mass of luliconazole; 2) 1 to 3% by mass of benzyl alcohol; and 3) 6 to 15% by mass of solvent selected from N-methyl-2-pyrrolidone, propylene carbonate and an ether of diethylene glycol in total; and is a transparent solution.

4. The pharmaceutical according to claim 3, wherein said pharmaceutical composition further comprises 10 to 16% by mass of a diester of a dibasic acid.

5. The pharmaceutical according to claim 3, wherein said pharmaceutical composition further comprises 3 to 6% by mass of an organic acid.

6. The pharmaceutical according to claim 5, wherein said organic acid is lactic acid.

7. A method for producing a pharmaceutical according to claim 5, comprising:
wetting luliconazole with a part of said solvent selected from N-methyl-2-pyrrolidone, propylene carbonate and an ether of diethylene glycol;
adding benzyl alcohol and an organic acid to, and dispersing, the wet luliconazole;
adding the remaining components to produce a pharmaceutical composition; and
filling obtained pharmaceutical composition in said resin container.

8. The pharmaceutical according to claim 1, wherein the material of said resin container is polypropylene or polyethylene.

9. The pharmaceutical according to claim 1, wherein said resin container is a bottle-shaped container.

10. The pharmaceutical according to claim 1, wherein said color is selected for the group consisting of Gray, Green and Brown.

11. The pharmaceutical according to claim 10, wherein said color is selected for the group consisting of Gray having a hue (H) of 7.56Y, value (V) of 5.0, and chroma (C) of 0.7; Green having a hue (H) of 9.46Y, value (V) of 2.1, and chroma (C) of 7.2; and Brown having a hue (H) of 8.4YR, value (V) of 1.7, and chroma (C) of 4.2.

* * * * *